(12) United States Patent
Hirschel et al.

(10) Patent No.: US 10,632,260 B2
(45) Date of Patent: Apr. 28, 2020

(54) CARPOULE HOLDER FOR RECEIVING A CARPOULE AND FASTENING TO A DRIVE MECHANISM AND/OR METERING MECHANISM AND/OR HOUSING OF AN INJECTION DEVICE

(71) Applicant: TecPharma Licensing AG, Burgdorf (CH)

(72) Inventors: Jürg Hirschel, Bern (CH); Ulrich Moser, Heimiswil (CH); Stefan Burren, Schwarezenburg (CH); Reto Bohner, Attiswil (CH); Bernhard Bigler, Huttwil (CH); Christian Schrul, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 15/684,280

(22) Filed: Aug. 23, 2017

(65) Prior Publication Data

US 2017/0348489 A1 Dec. 7, 2017

Related U.S. Application Data

(63) Continuation of application No. PCT/CH2016/000021, filed on Jan. 28, 2016.

(30) Foreign Application Priority Data

Feb. 26, 2015 (CH) .................................. 260/15

(51) Int. Cl.
 *A61M 5/24* (2006.01)

(52) U.S. Cl.
 CPC ....... *A61M 5/24* (2013.01); *A61M 2005/2407* (2013.01); *A61M 2005/2477* (2013.01); *A61M 2005/2485* (2013.01); *A61M 2207/00* (2013.01)

(58) Field of Classification Search
 CPC .. A61M 2005/2407; A61M 2005/2477; A61M 2005/2485; A61M 2207/00; A61M 5/24
 See application file for complete search history.

(56) References Cited

U.S. PATENT DOCUMENTS 1,718,600 A  6/1929  Smith
1,718,602 A  6/1929  Smith
(Continued)

FOREIGN PATENT DOCUMENTS

WO  2001060311 A1  8/2001
WO  2010043533 A1  4/2010
(Continued)

OTHER PUBLICATIONS

PCT International Search Report dated Jun. 1, 2016, for Application No. PCT/CH2016/000021, 6 pages.
(Continued)

*Primary Examiner* — Imani N Hayman
(74) *Attorney, Agent, or Firm* — Dorsey & Whitney LLP

(57) ABSTRACT

The invention relates to a carpoule holder (8) for receiving a carpoule (10) and for fastening to a drive mechanism and/or to a dosing mechanism and/or to a housing (6) of an injection device, with a holding element (9, 9', 9") for fastening the carpoule (10) to or in the carpoule holder (8), wherein the holding element (9, 9', 9") is designed in such a way that it can be connected to the carpoule holder (8) and can be received completely by the carpoule holder (8).

20 Claims, 12 Drawing Sheets

(56) References Cited

U.S. PATENT DOCUMENTS

2007/0021718 A1     1/2007   Burren et al.
2010/0137809 A1*    6/2010   Tschirren ............... A61M 5/24
                                                        604/187

FOREIGN PATENT DOCUMENTS

WO      2012017035 A1    2/2012
WO      2014066256 A1    5/2014

OTHER PUBLICATIONS

PCT International Preliminary Report on Patentability dated Aug. 29, 2017 for Application No. PCT/CH2016/000021, 8 pages.

* cited by examiner

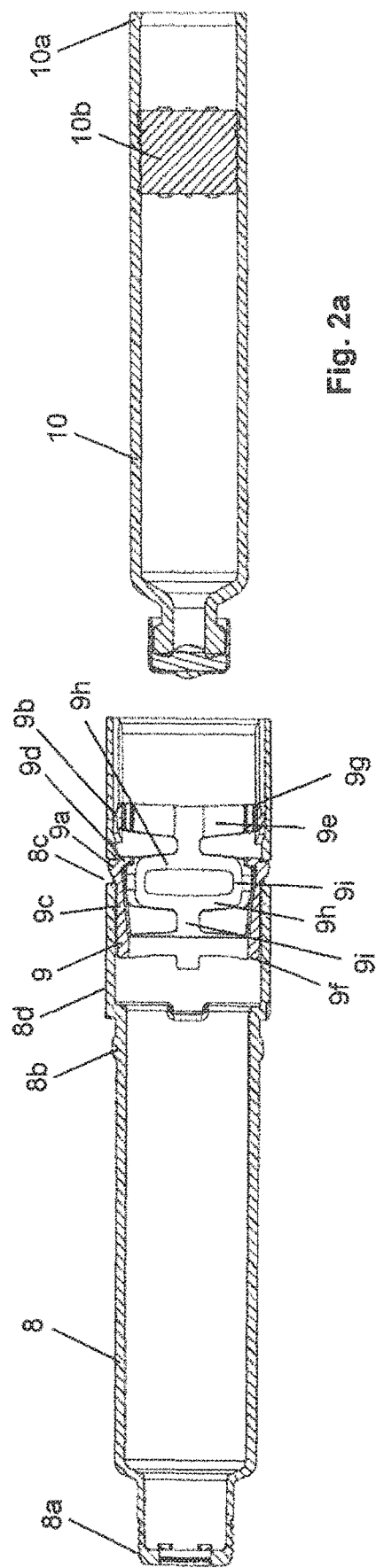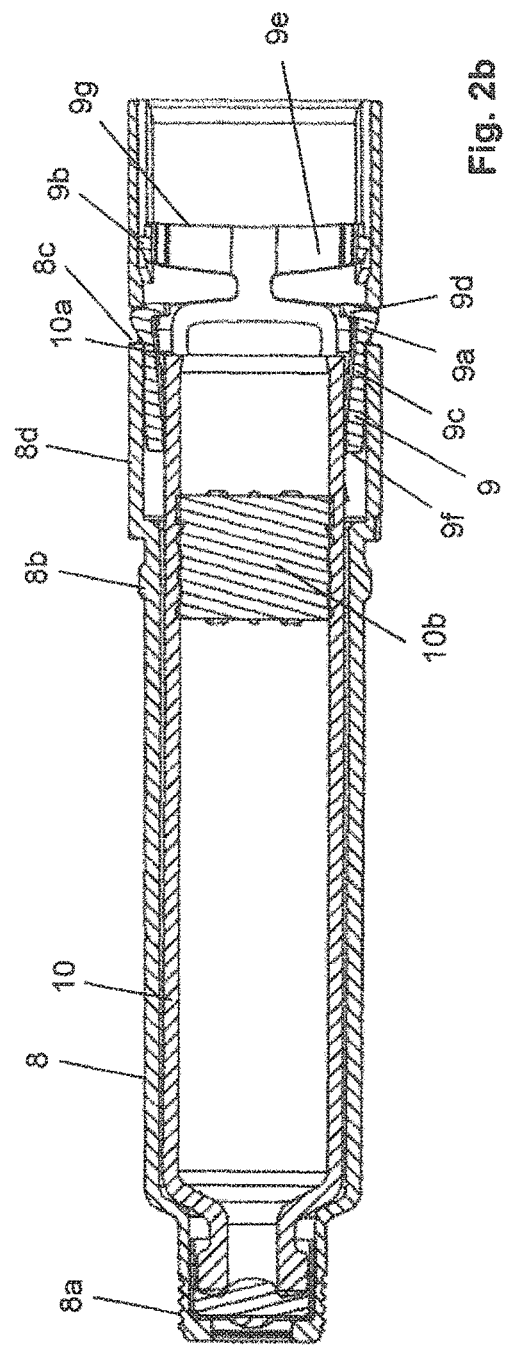

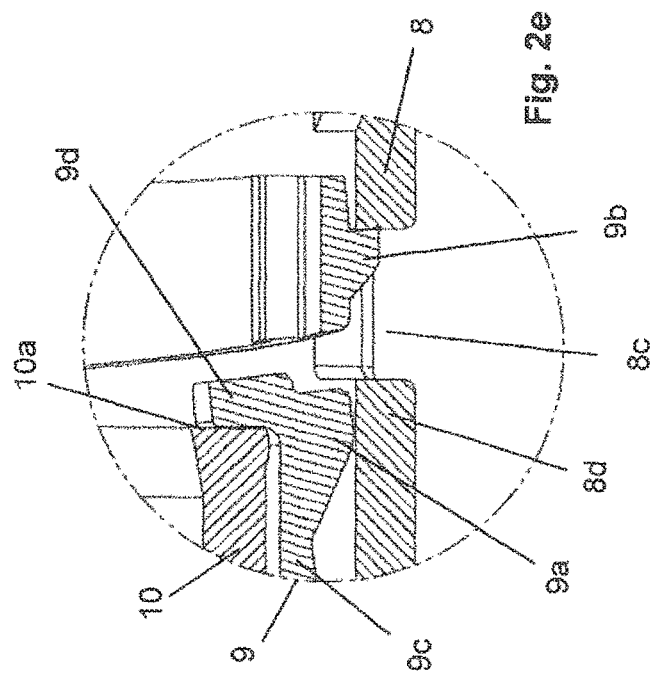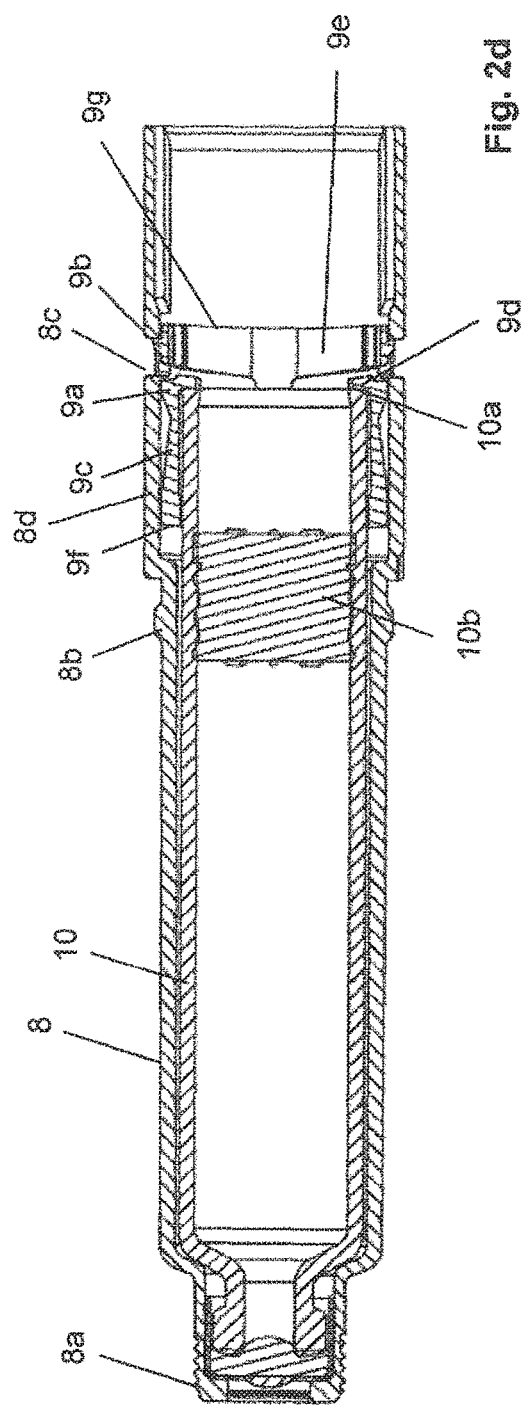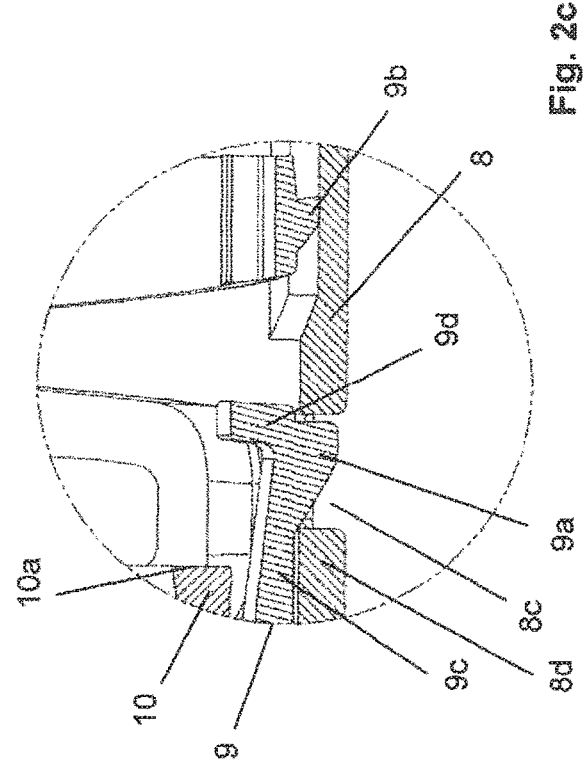

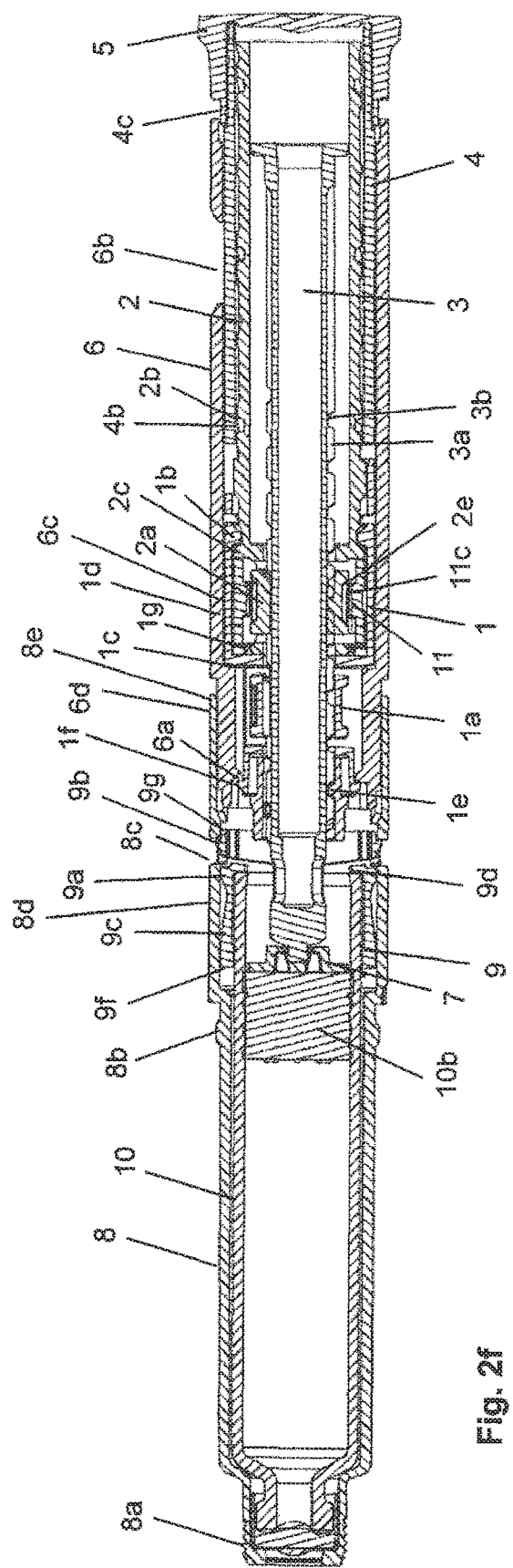
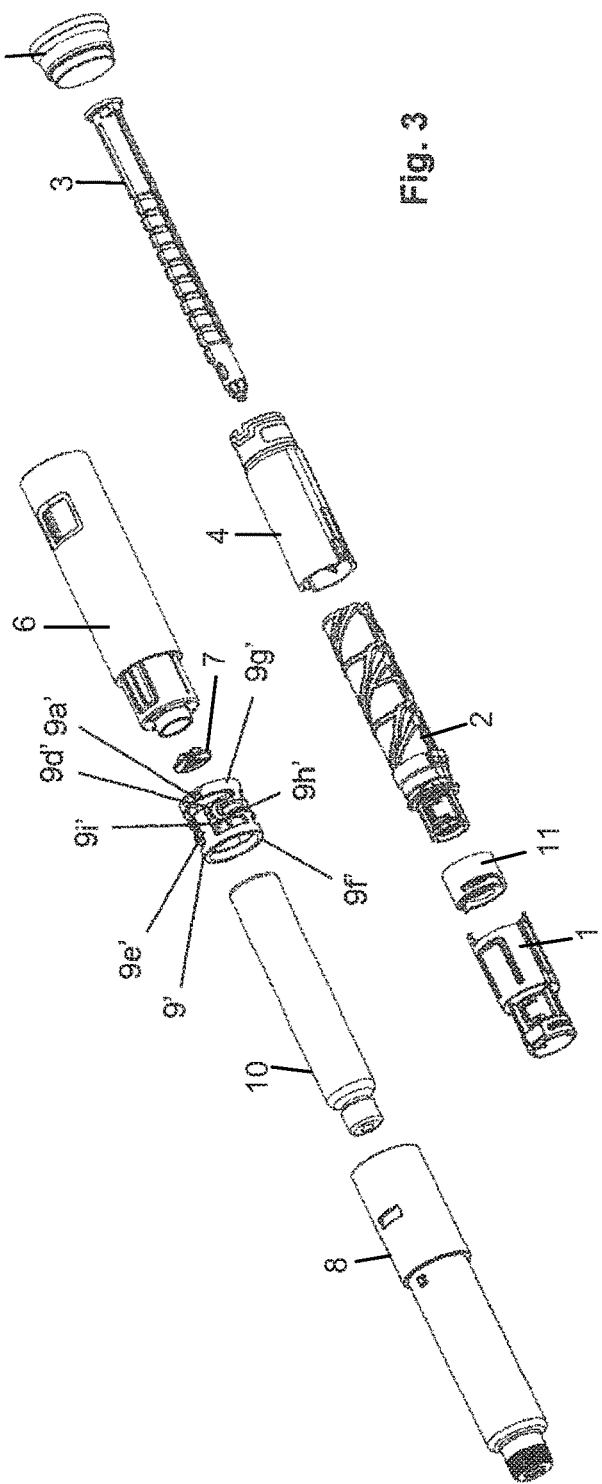

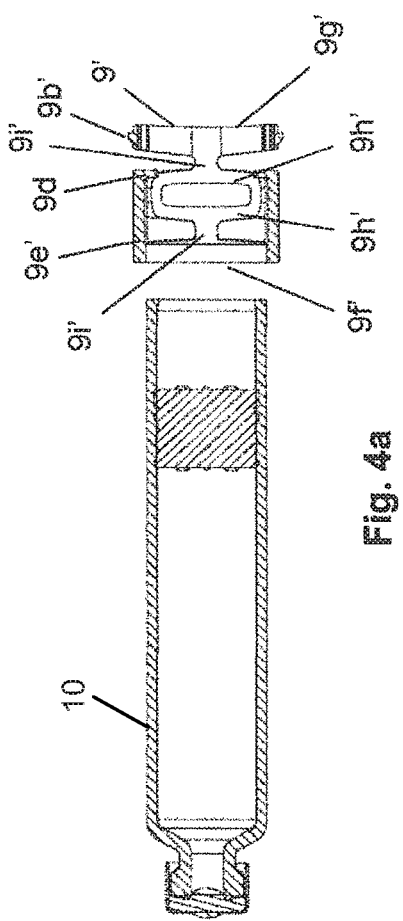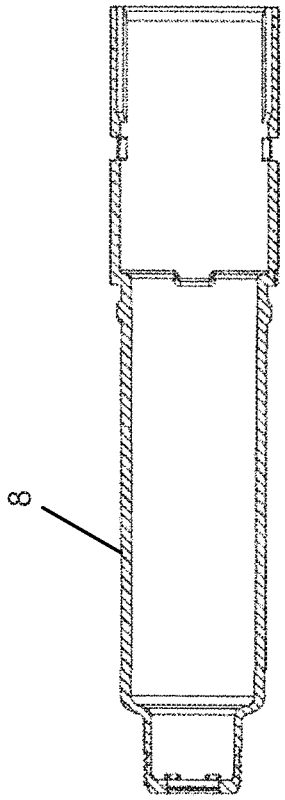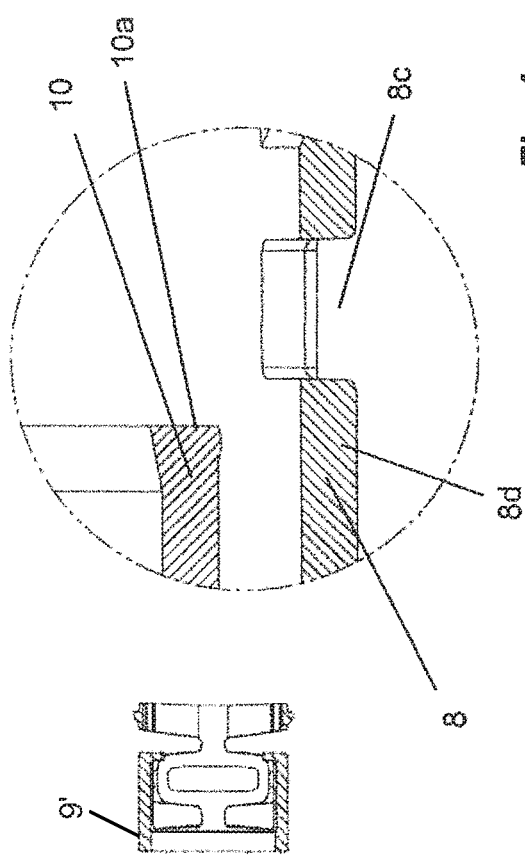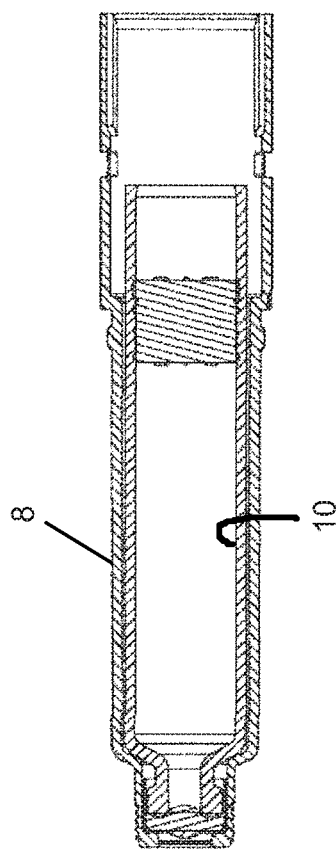

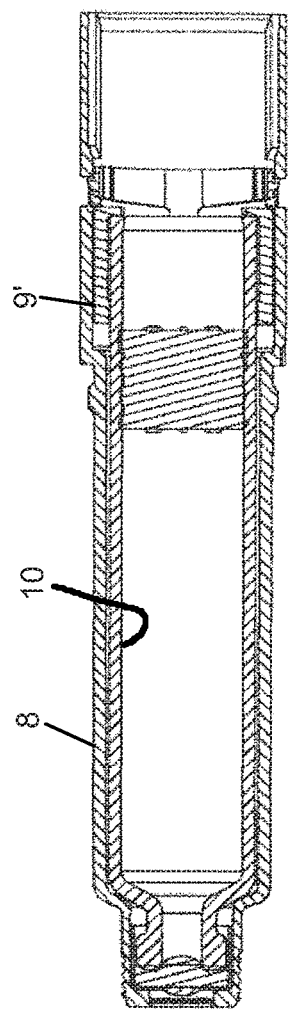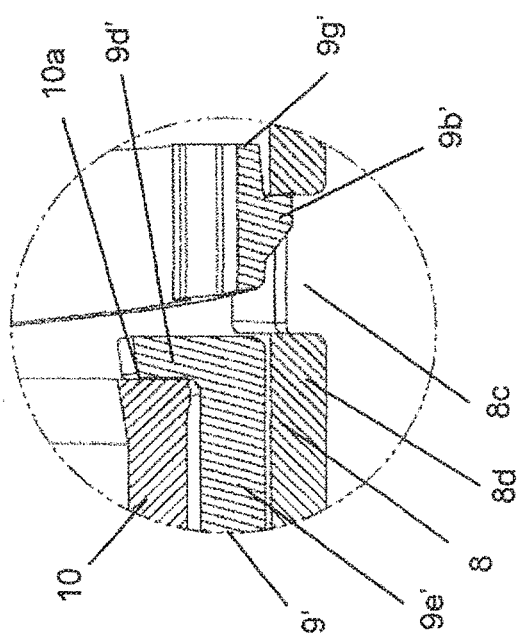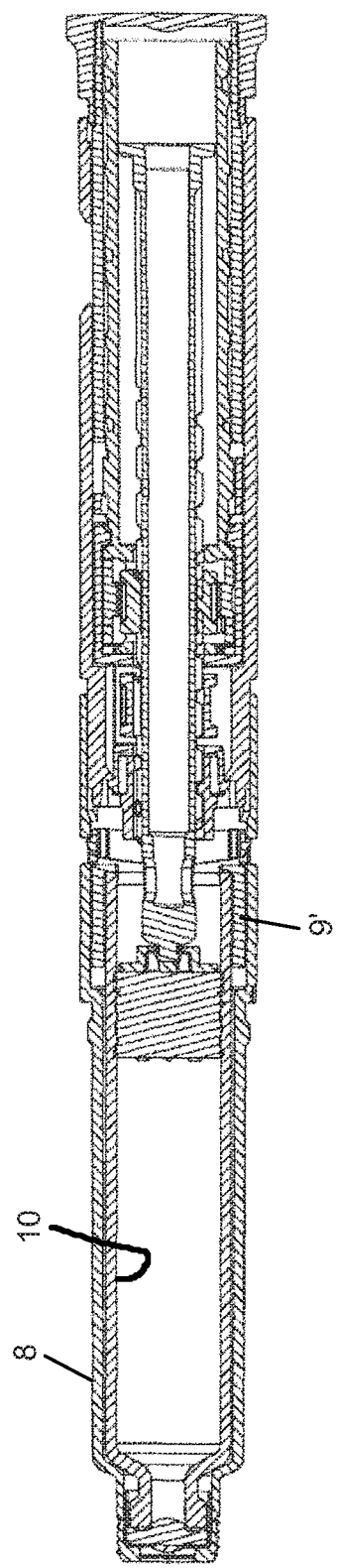
Fig. 4d
Fig. 4e
Fig. 4f

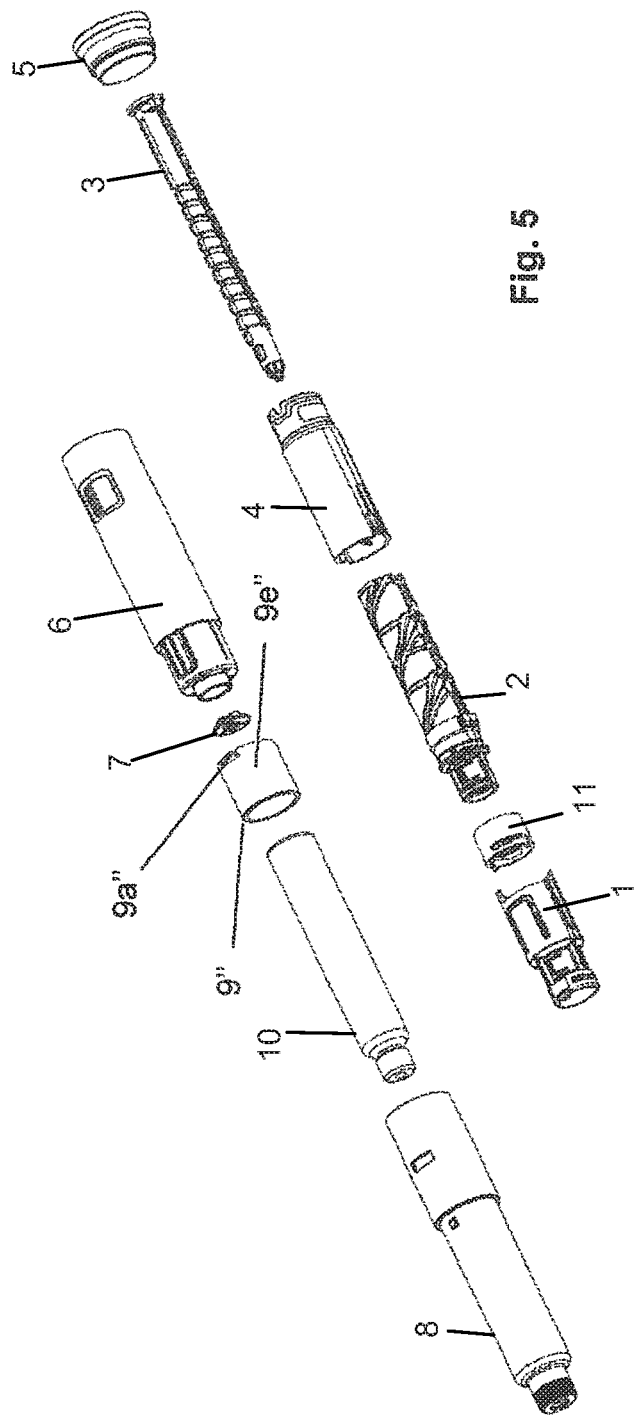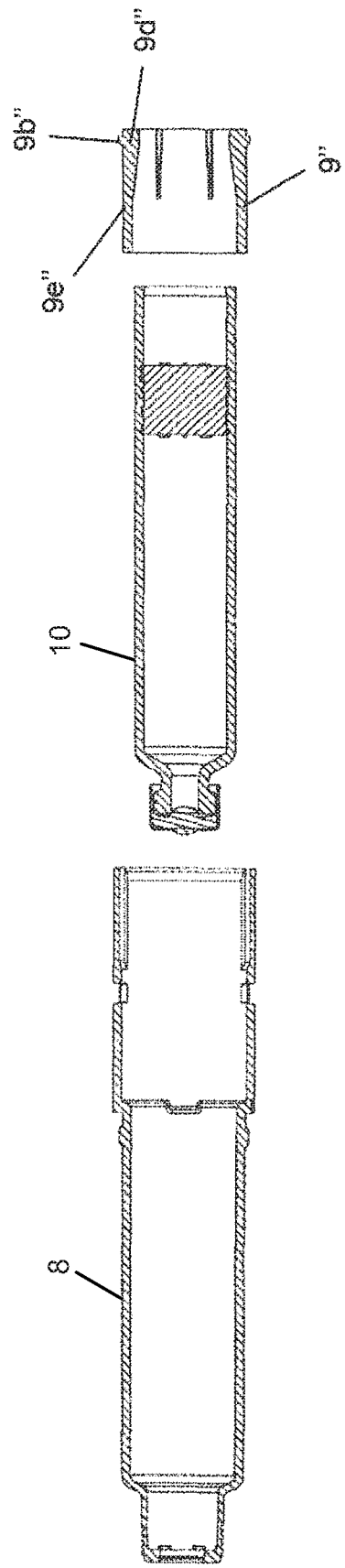

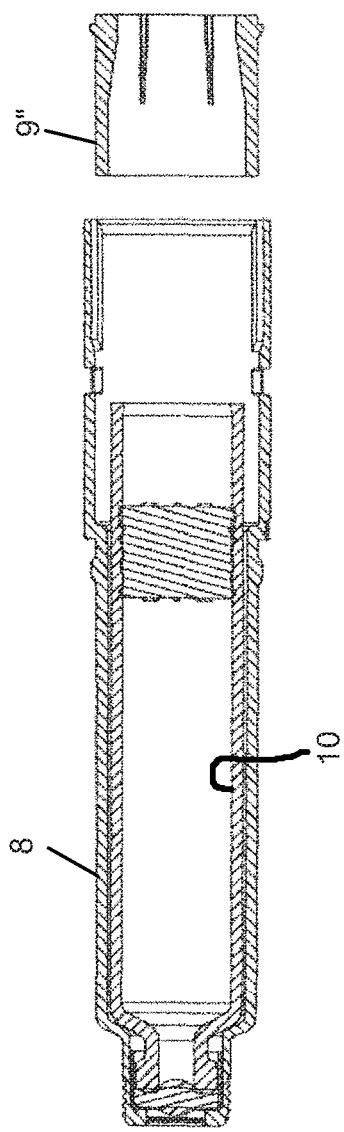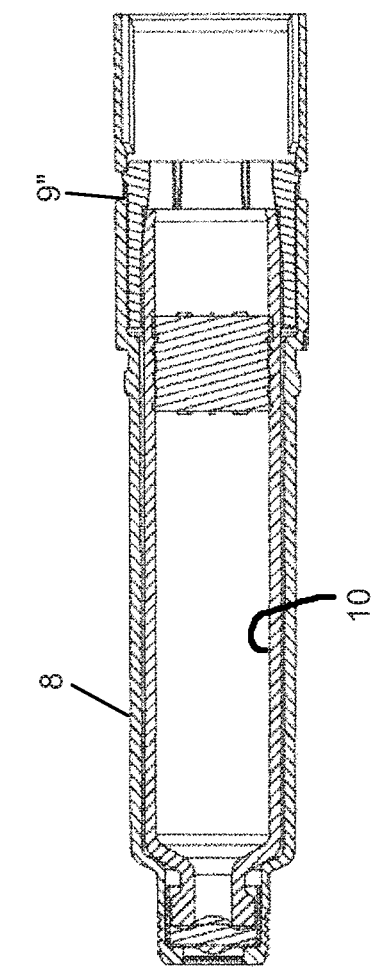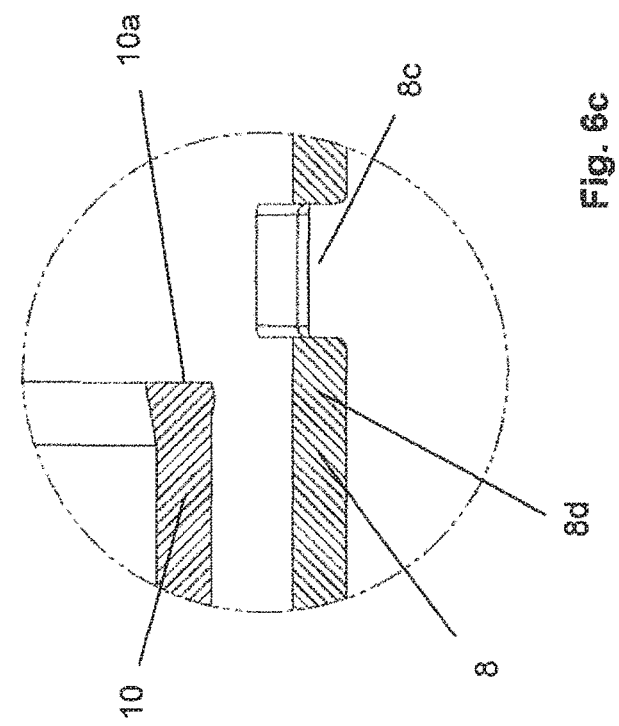

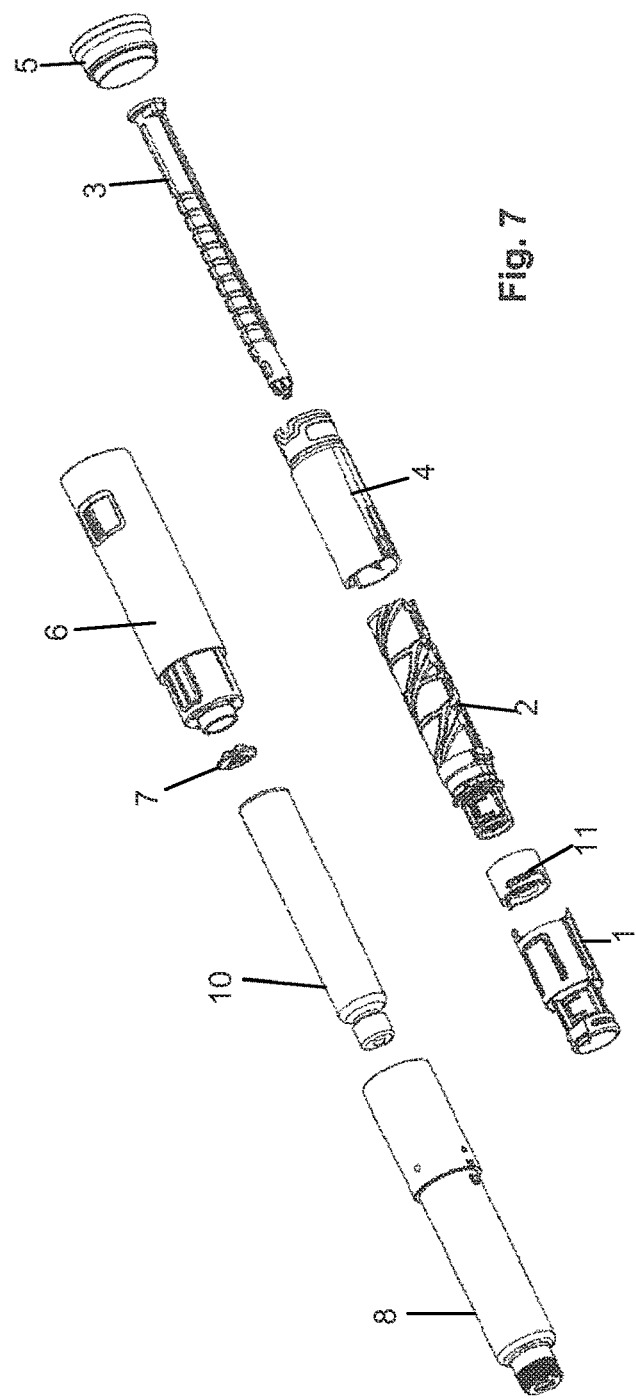
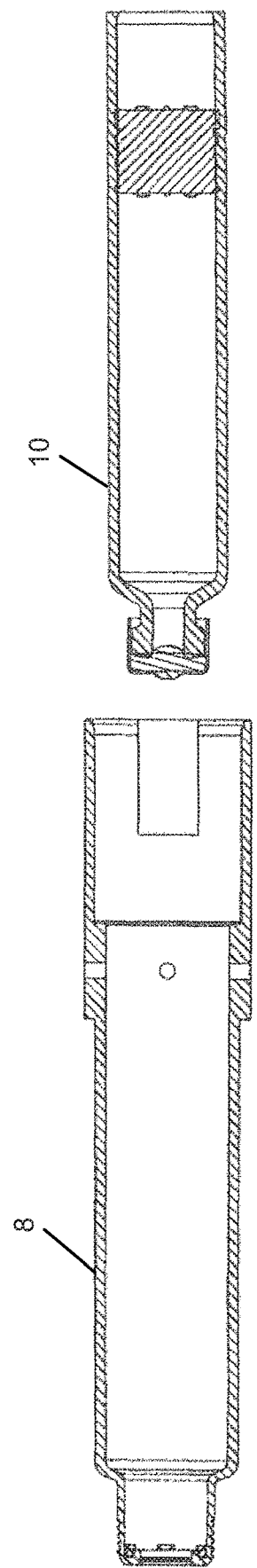
Fig. 7
Fig. 8a

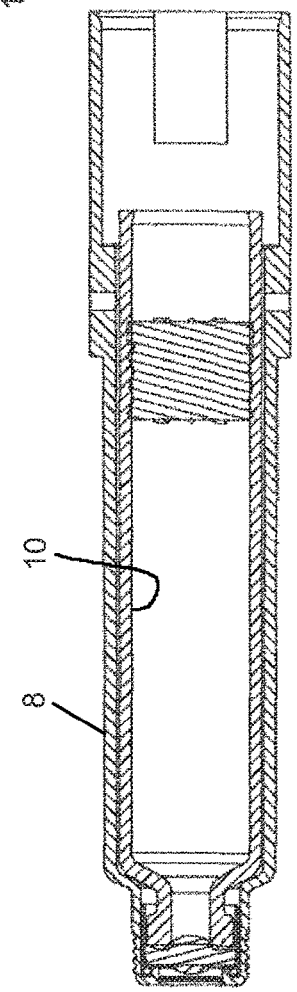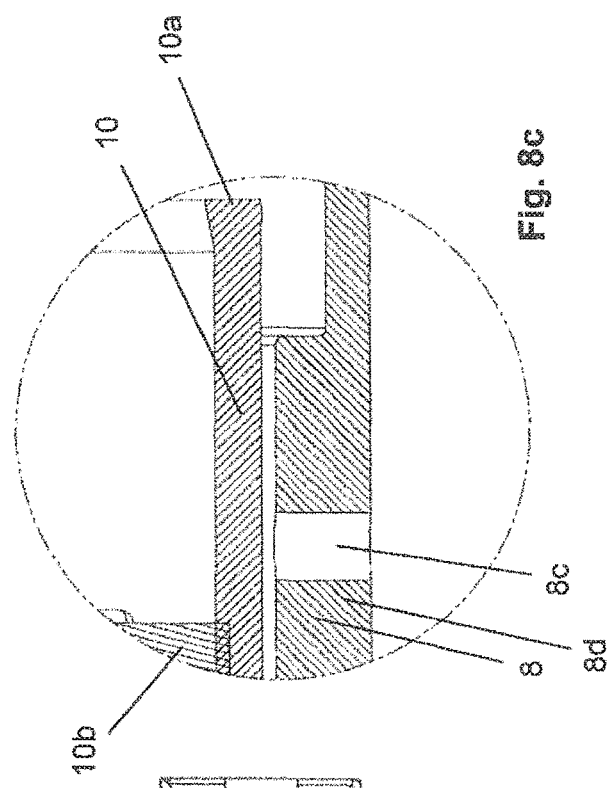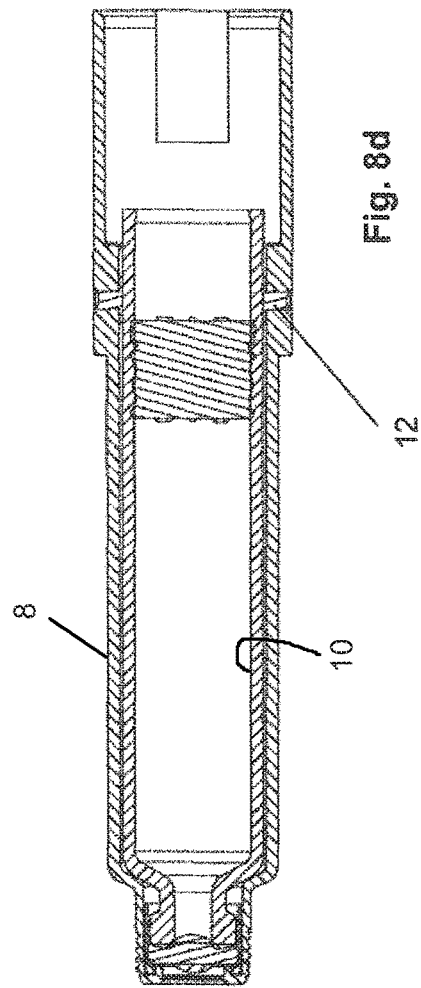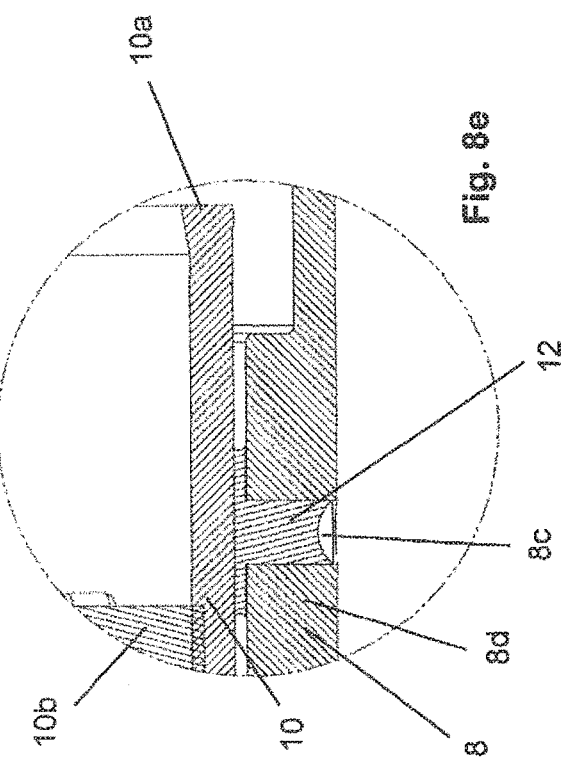

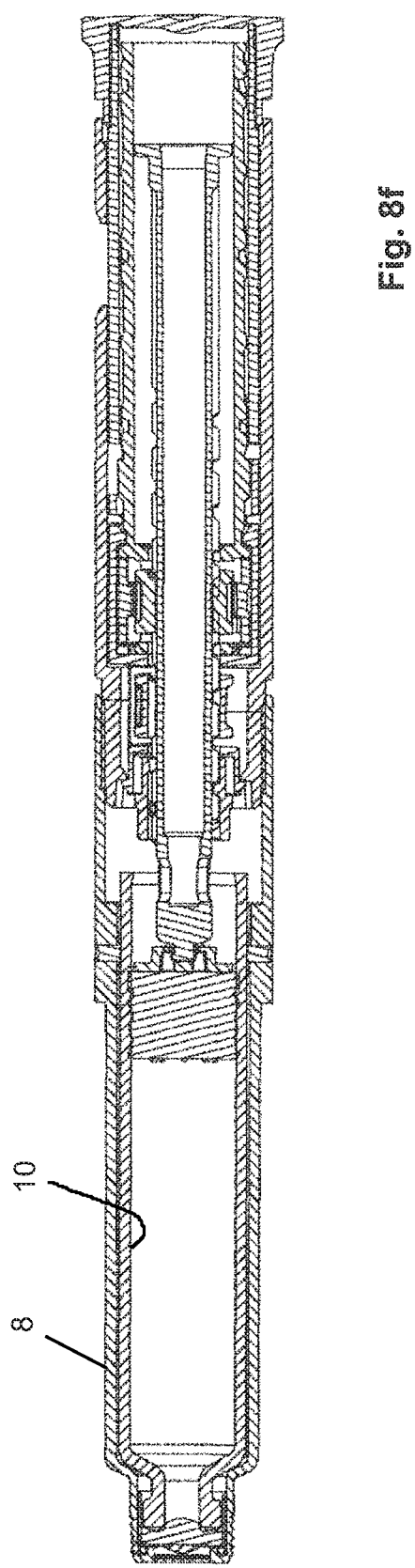

CARPOULE HOLDER FOR RECEIVING A CARPOULE AND FASTENING TO A DRIVE MECHANISM AND/OR METERING MECHANISM AND/OR HOUSING OF AN INJECTION DEVICE

CROSS-REFERENCE TO RELATED APPLICATIONS

This application is a continuation of International Application No. PCT/CH2016/000021 filed Jan. 28, 2016, which claims priority to Swiss Application No. 260/15 filed Feb. 26, 2015, the contents of all of which are herein incorporated by reference.

BACKGROUND

The present invention relates to a carpoule holder for receiving a carpoule and fastening it to a drive mechanism and/or metering mechanism and/or housing of an injection device; to an injection device for administering a fluid product, particularly a drug such as teriparatide for osteoporosis therapy; and to a method for mounting a carpoule in a carpoule holder. The injection device connected to the carpoule holder may be used for metering in and administering a specified dose.

The term "drug" as used herein encompasses any fluid pharmaceutical formulation suitable for controlled administration by a means such as a cannula or hollow needle, for example a liquid, a solution, a gel or a fine suspension, comprising one or more pharmaceutical active ingredients. A drug may be a composition having a single active ingredient or may be a premixed or co-formulated composition having multiple active ingredients in a single container. Drugs encompass such medications as peptides (e.g., insulin-containing medications, glutamine-containing medications, GLP-1-containing preparations and those derived from or analogous thereto), proteins and hormones, biologically derived or biologically active substances, active ingredients based on hormones or genes, nutrient isolates, enzymes and other substances both in solid (suspended) or liquid form, as well as polysaccharides, vaccines, DNA or RNA or oligonucleotides, antibodies or parts of antibodies, and suitable bases, adjuvants and carriers.

WO2012/017035A1 discloses a carpoule holder for a drug administration device, wherein the carpoule is fastened in the carpoule holder by means of a clamping element.

SUMMARY OF THE INVENTION

One purpose of the present invention is to provide an alternative carpoule holder for receiving a carpoule, wherein a carpoule may be fastened to the carpoule holder, and in particular may be held fixedly in place, thereby enhancing the metering accuracy of the injection device.

Another purpose of the present invention is to provide a method for assembling a carpoule onto or in a carpoule holder, wherein in particular the carpoule is held fixedly in the carpoule holder.

These purposes are achieved as set forth in the independent claims. The dependent claims set forth advantageous embodiments.

As used herein, "distal" means a direction toward the end of the carpoule holder nearest the injection-needle and proximal to the drive mechanism and/or the metering mechanism and/or the housing.

The invention relates to a carpoule holder for receiving a carpoule and for fastening to a drive mechanism and/or to a metering mechanism and/or to a housing of an injection device. Further, the carpoule holder has a holding element for fastening the carpoule to or in the carpoule holder, wherein the holding element is configured in such a way that it may be connected to the carpoule holder and may be received completely by the carpoule holder.

The holding element is a component of the carpoule holder. The holding element has a holding and/or fixing and/or positioning function. The holding element may, for example, be formed from plastic. Furthermore, the holding element may be elastically deformable. The holding element may comprise a cam. This cam may project radially outward. Furthermore, the holding element may preferably be furnished with a clamping element. The clamping element may project radially inward, in order to hold, clamp, or grasp the carpoule inserted into the carpoule holder, in particular a proximal end of the carpoule.

The carpoule holder may comprise a carpoule holder housing, in particular a cylindrical carpoule holder housing. The holding element may be completely received or accommodated by the carpoule holder housing of the carpoule holder. The holding element is mounted in the carpoule holder housing so that it may be moved axially. Alternatively, the carpoule holder housing may have a different configuration. The carpoule holder housing is configured in such a way that a carpoule may be received in the carpoule holder housing.

The carpoule holder housing and the holding element of the carpoule holder are configured in two parts. Preferably, the carpoule holder housing and the holding element are made of different materials. The carpoule holder housing and the holding element may be made of plastic, in which case the carpoule holder housing is preferably non-deformable and the holding element is preferably elastically deformable. All components of the holding element may preferably be elastically deformable.

The holding element may be used for holding and/or fixing and/or positioning a component of the injection device on or in another component: the holding element in a tensioned state holds one of the components in a particular position relative to the other, e.g. holding one component in tension so as to maintain abutting contact with the other component. The holding element may thus hold a component of the injection device in a defined position inside the injection device. The defined position is determined by the spatial arrangement of the component to be held, relative to another component of the injection device. The components may be a carpoule in a carpoule holder. The carpoule may preferably be held fixedly on or in the carpoule holder by means of a holding element, by holding the carpoule in the carpoule holder by axial abutting contact on the distal side and by means of the holding element on the proximal side. Manufacturing and assembly tolerances may be compensated for in this way.

The holding element may be furnished with a ring element. The ring element may be realized with a ring shape or sleeve shape. The ring element may also preferably be realized with a cylindrical shape. A first and a second spring seat may be furnished on the ring element. The ring element may comprise a plurality of brackets and a plurality of connecting bridges, and the first spring seat may be connected to the second spring seat via the plurality of brackets and the plurality of connecting bridges. The brackets and preferably the connecting bridges are elastically deformable in the axial direction. Alternatively, the connecting bridges may be axially rigid. The brackets extend in the circumferential direction, and are realized as curved toward the distal or proximal side. The first spring seat may be connected to a first bracket via a first connecting bridge, and the first bracket may be connected to a second bracket via a second connecting bridge, and the second bracket may be connected to the second spring seat via a second connecting bridge. The first and second brackets may form elastic bending arms. The first and second brackets thus project from the first and second spring seats above the connecting bridges in the axial direction. Alternatively, a different number of brackets, connecting bridges and spring seats may also be provided on the holding element. Further, the ring element may also have a different configuration, if the ring element may be subjected to pressure along the axial axis.

The carpoule holder may additionally hold the holding element at least partially in an annular gap between the carpoule holder and the carpoule, in a first position wherein the carpoule is movably received in the carpoule holder, and in a second position wherein the carpoule is received and fastened in the carpoule holder. The holding element is configured in such a way that in the second position, the holding element may hold the carpoule fixedly axially relative to the carpoule holder. The carpoule may then be supported in the distal direction on or in the carpoule holder and in the proximal direction on the holding element.

In one embodiment, a projection may also be provided on the holding element, which is connected to the holding element via a spring element. The projection may project radially outward; in that case, the clamping element, which is likewise arranged on a spring element, projects radially inward. Furthermore, in the first position, the projection of the holding element may project into the recess of the carpoule holder, so as to connect the holding element to the carpoule holder. Furthermore, in the first position, the holding element is inserted into the carpoule holder by virtue of the projection of the holding element being locked into the recess of the carpoule holder. The connection between the projection of the holding element and the recess of the carpoule holder is configured so that these may be disengaged from one another. In the second position, the projection of the holding element is pushed out of the recess of the carpoule holder, and the cam of the holding element, which is arranged on the second spring seat, engages in the recess of the carpoule holder, so as to elastically tension the holding element. The connection between the cam and the recess of the carpoule holder may be configured so as to be non-detachable. This non-detachable connection may be realized in a form-fitting manner, so that the holding element may as a result be elastically tensioned in the axial and radial directions. The cam of the holding element may project radially outward. In addition, the clamping element of the holding element may hold or clamp a proximal edge of the carpoule in the second position. The carpoule is held fixedly in the carpoule holder, between the carpoule holder and the holding element.

In one configuration, the holding element is inserted into the carpoule holder housing of the carpoule holder in the first position, and the holding element is arranged in the carpoule holder housing in such a way that a carpoule may be introduced into the carpoule holder housing. The carpoule holder may thus be transported in the first position, for example as an assembly unit, and a carpoule may be inserted into the carpoule holder in the first position at another location, for example an assembly location. The carpoule holder inserted with the carpoule may, for example, be moved from the first position to the second position at the assembly location by means of an axial force acting in the distal direction, and acting on the holding element of the carpoule holder. In the second position, the carpoule is held in the carpoule holder, and in particular is held there axially and in a fixed position. The carpoule may then no longer be removed from the carpoule holder.

The holding element received in the carpoule holder housing of the carpoule holder, in the second position, is arranged offset relative to the first position. An axial force that may act on a spring seat of the holding element, may result in the holding element being displaced in the axial direction relative to the carpoule holder housing. Preferably, the axial force acts in the distal direction such that the holding element is moved distally from the first position to the second position. A tool, e.g. a pressing or pushing device, may act on a spring seat of the holding element, in particular the second spring seat of the holding element, in such a way that the holding element is moved in the axial direction relative to the carpoule holder housing.

In another embodiment, the holding element may be inserted into a carpoule holder housing in which a carpoule has been received. The holding element may comprise a cam disposed on a spring seat, in particular the second spring seat, and a clamping element furnished on a ring element. In order to insert the holding element into the carpoule holder so that the carpoule may be held within the carpoule holder, the cam of the holding element may engage in a recess of the carpoule holder housing, with a clamping element holding or clamping a proximal edge of the carpoule. The cam of the holding element may form a non-detachable connection with the recess, and in particular may be realized in a form-fitting way. The holding element is in that case tensioned in the axial, in particular distal direction; the holding of the carpoule in the carpoule holder is achieved by a clamping fit or by a clamping seat.

In another embodiment, the holding element may also be inserted into a carpoule holder housing in which a carpoule has been received. The holding element may comprise a ring element in the form of a cylinder. In that case, the ring element consequently does not have a bracket, a connecting bridge, or a spring seat. When the holding element is inserted into a carpoule holder that has received a carpoule, the cam of the holding element may engage in a recess of the carpoule holder housing, and a clamping element of the holding element may clamp the carpoule onto or into the carpoule holder.

The cam of the holding element may engage in the recess of the carpoule holder, and the connection may be so configured as to be non-detachable, and in particular form-fitting.

In an alternative embodiment, the carpoule may be glued or welded onto or into the carpoule holder. In this embodiment, the adhesive or the weld replaces the holding element. In particular, a holding element that is configured to be elastically deformable is not required. If the carpoule is in axial, in particular distal, abutting contact with the carpoule holder, the carpoule is adhered or welded to the carpoule holder. The connection between the carpoule and the carpoule holder may be configured so as to be non-detachable. The adhesive or welded connection between the carpoule and the carpoule holder may be configured as a force-fit.

In an alternative embodiment, the carpoule and the carpoule holder may be held with the aid of a form-fit. If, for example, the carpoule is in axial, and in particular in distal, abutting contact with the carpoule holder, an inwardly projecting holding element may be mounted on an inner side of the carpoule holder housing in such a way that the carpoule is held in the carpoule holder, and in particular is held fixedly. The holding element may be elastically deformable or elastically non-deformable. The holding element may be non-detachably connected to the carpoule holder. The connection between the holding element and the carpoule holder may be realized as a force-fit or form-fit. The holding element may be an adhesive or a fastening means. Preferably, the holding element may be one or more drops of adhesive. The one or more adhesive drops may be placed on the inner side of the carpoule holder housing, after the carpoule has been introduced into the carpoule holder. The one or more adhesive drops are preferably arranged at a proximal edge of the carpoule. The adhesive or fastening means may form an axial, and in particular a proximal, abutting contact. Alternatively, the adhesive or the fastening means may hold the carpoule in the carpoule holder by force-fit or form-fit, and in particular may hold it fixedly.

The invention also relates to a method for assembling a carpoule onto or into a carpoule holder such that in particular the carpoule is held fixedly in the carpoule holder. In this case, a holding element may first be introduced into the carpoule holder. The carpoule holder preferably comprises a carpoule holder housing, in which a recess is furnished, wherein a projection attached to the holding element, engages in the recess of the carpoule holder. The carpoule may be inserted into a carpoule holder that is furnished with the holding element. The carpoule is in axial abutting contact with the carpoule holder on its distal side. The holding element is offset relative to the carpoule holder, and in particular the carpoule holder housing, by means of an axial force acting in the distal direction, for example in the form of a tool, for example with the aid of a pressing or pushing device, such that the projection of the holding element is pushed out of the recess of the carpoule holder, and a cam of the holding element engages in the recess of the carpoule holder so as to elastically tension the holding element.

In this case, the holding element may be tensioned in the axial and radial direction, such that the carpoule is connected fixedly to the carpoule holder, with a clamping element of the holding element holding or clamping a proximal edge of the carpoule. The carpoule is held in the carpoule holder on the proximal side, with the aid of the holding element.

BRIEF DESCRIPTION OF THE DRAWINGS

FIG. 2a is a longitudinal cross section of the first embodiment of the carpoule holder in an initial position, wherein the carpoule has not been received in the carpoule holder.

FIG. 2b is a longitudinal cross section of the first embodiment of the carpoule holder in a first position, wherein the carpoule has been movably received in the carpoule holder.

FIG. 2c is a detail view of FIG. 2b.

FIG. 2d is a longitudinal cross section of the first embodiment of the carpoule holder in a second position, wherein the carpoule has been fixedly received in the carpoule holder.

FIG. 2e is a detail view of FIG. 2d.

FIG. 2f is a longitudinal cross section of the injection device with the first embodiment of the carpoule holder in which the carpoule has been received and fastened, wherein the carpoule holder is axially fixedly connected to the housing of the injection device for metering and administering a fixed dose of a fluid product.

FIG. 3 is an exploded view of an injection device for metering and administering a fixed dose of a fluid product using a second embodiment of a carpoule holder.

FIG. 4a is a longitudinal cross section of the second embodiment of the carpoule holder in an initial position, wherein the carpoule has not been received in the carpoule holder.

FIG. 4b is a longitudinal cross section of the second embodiment of the carpoule holder in a first position, wherein the carpoule has been movably received in the carpoule holder.

FIG. 4c is a detail view of FIG. 4b.

FIG. 4d is a longitudinal cross section of the second embodiment of the carpoule holder in a second position, wherein the carpoule has been fixedly received in the carpoule holder.

FIG. 4e is a detail view of FIG. 4d.

FIG. 4f is a longitudinal cross section of the injection device with the second embodiment of the carpoule holder in which the carpoule has been received and fastened, wherein the carpoule holder is axially fixedly connected to the housing of the injection device for metering and administering a fixed dose of a fluid product.

FIG. 5 is an exploded view of an injection device for metering and administering a fixed dose of a fluid product using a third embodiment of a carpoule holder.

FIG. 6a is a longitudinal cross section of the third embodiment of the carpoule holder in an initial position, wherein the carpoule has not been received in the carpoule holder.

FIG. 6b is a longitudinal cross section of the third embodiment of the carpoule holder in a first position, wherein the carpoule has been movably received in the carpoule holder.

FIG. 6c is a detail view of FIG. 6b.

FIG. 6d is a longitudinal cross section of the third embodiment of the carpoule holder in a second position, wherein the carpoule has been fixedly received in the carpoule holder.

FIG. 7 is an exploded view of an injection device for metering and administering a fixed dose of a fluid product using a fourth embodiment of a carpoule holder.

FIG. 8a is a longitudinal cross section of the fourth embodiment of the carpoule holder in an initial position, wherein the carpoule has not been received in the carpoule holder.

FIG. 8b is a longitudinal cross section of the fourth embodiment of the carpoule holder in a first position, wherein the carpoule has been movably received in the carpoule holder.

FIG. 8c is a detail view of FIG. 8b.

FIG. 8d is a longitudinal cross section of the fourth embodiment of the carpoule holder in a second position, wherein the carpoule has been fixedly received in the carpoule holder.

FIG. 8e is a detail view of FIG. 8d.

FIG. 8f is a longitudinal cross section of the injection device with the fourth embodiment of the carpoule holder in which the carpoule has been received and fastened, wherein the carpoule holder is axially fixedly connected to the housing of the injection device for metering and administering a fixed dose of a fluid product.

DETAILED DESCRIPTION

Figure 1:
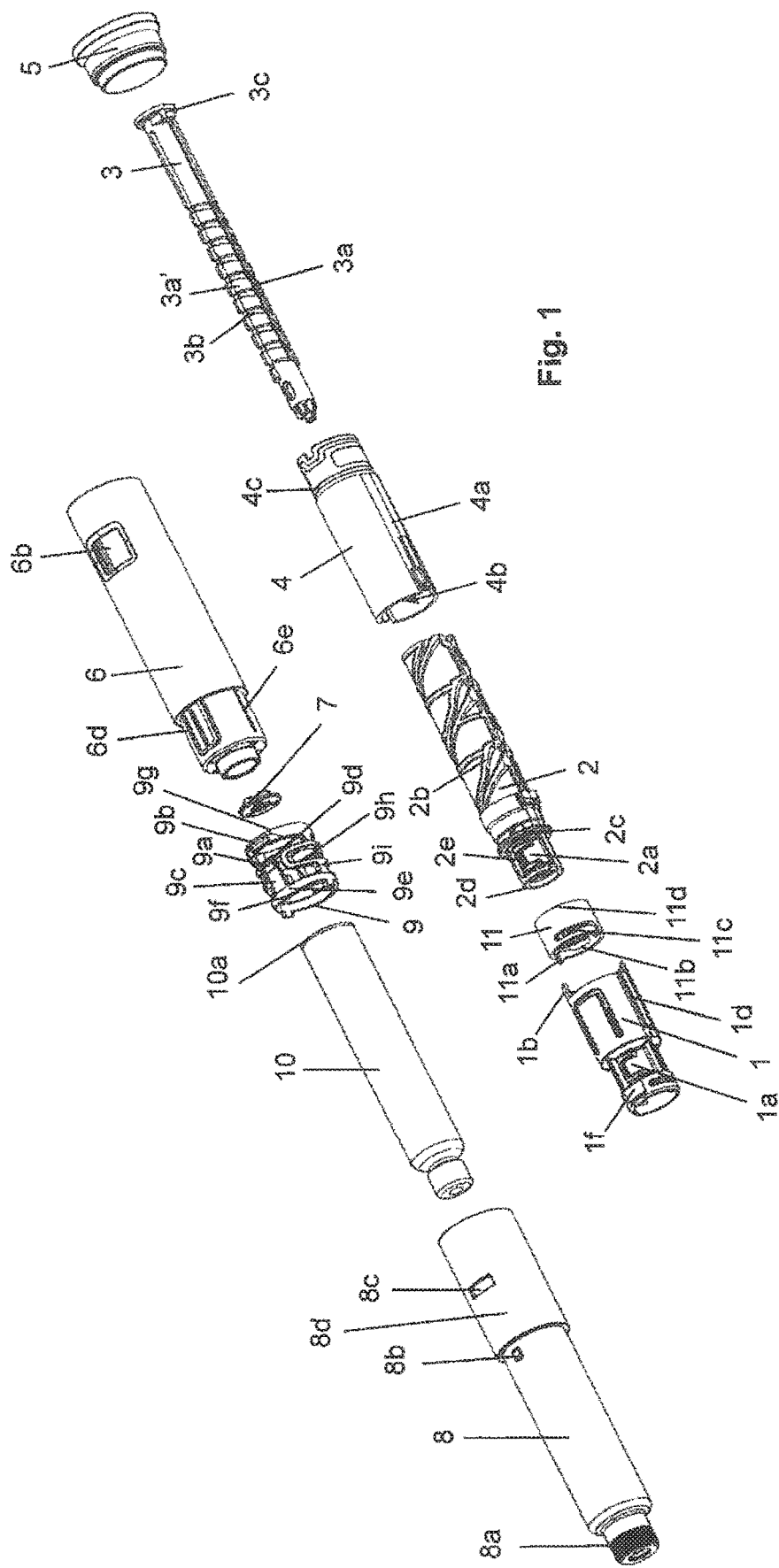
FIG. 1 is an exploded view of an injection device for metering and administering a fixed dose of a fluid product using a first embodiment of a carpoule holder.

FIG. 1 shows an exploded view of a first embodiment of the injection device according to this invention. The injection device comprises a carpoule holder (8) that may receive a carpoule (10); the carpoule holder (8) may be axially fixedly connected to a housing (6).

This connection may be realized as an adhesive connection or a welded connection. The housing (6) may preferably have a housing guide ring (6d), which may engage with a carpoule holding guide groove (8e, see e.g. FIG. 2f) that is arranged on the carpoule holder (8). Furthermore, the housing (6) may have a housing bridge (6e), preferably a plurality of housing bridges (6e). A needle connecting element (8a) is furnished at the distal end of the carpoule holder (8), for detachably fastening an injection needle (not shown). The injection device further comprises a closure cap (not shown), which may be connected to the carpoule holder (8) via a detachable connection. For this purpose, the carpoule holder (8) has a carpoule holder projection (8b) that may engage in an annular groove (not shown) of the closure cap (not shown). Preferably, the annular groove (not shown) of the closure cap (not shown) may have a depression, such that the closure cap (not shown) may be arranged in a rotationally fixed manner relative to the carpoule holder (8). The carpoule holder (8) further comprises a carpoule holder housing (8d) in which is arranged a recess (8c) for receiving a projection (9a) and a cam (9b) of a holding element (9). The holding element (9) is elastically deformable. The holding element (9) comprises a spring element (9c), on which are furnished the projection (9a) and a clamping element (9d). The holding element (9) has a ring element (9e), which comprises a first spring seat (9f), a second spring seat (9g), a plurality of brackets (9h) and a plurality of connecting bridges (9i); the first spring seat (9f) is connected to the second spring seat (9g) via the plurality of brackets (9h) and the plurality of connecting bridges (9i). The injection device also comprises a guide sleeve (1). The guide sleeve (1) is secured to the housing (6) and prevented from rotating by a guide sleeve bridge (1d) attached to the guide sleeve (1) and a groove (6c; see e.g. FIG. 2f) on the housing (6), and is held in place axially by an inwardly projecting guide sleeve projection (1f) of the guide sleeve (1) and a housing holding arm (6a, see e.g. FIG. 2f) that is attached to the housing (6). The guide sleeve (1) has an engaging element (1a) that may interact with the toothing of the threaded rod (3). The injection device further comprises a rotary sleeve (2) that is connected to the guide sleeve (1) so as to be rotatable and axially fixed. For this purpose, the rotary sleeve (2) has a rotary sleeve ring bridge (2c), which may axially abut the proximal side of the guide sleeve holding arm (1b), and preferably of two guide sleeve holding arms (1b); the rotary sleeve edge (2d) may additionally establish axial abutting contact with a guide sleeve front (1c, see e.g. FIG. 2f) of the guide sleeve (1). The rotary sleeve (2) also comprises an engagement element (2a) that may interact with the toothing of the threaded rod (3). The toothing of the threaded rod (3) comprises a tooth (3a), preferably a plurality of teeth, and especially preferably four teeth. Furthermore, the threaded rod (3) has an external thread (3b) that forms a threaded connection with an internal thread (1e, see e.g. FIG. 2f) of the guide sleeve (1). The engagement mechanism of the engagement elements (2a, 1a) that engages the rotary sleeve (2) and guide sleeve (1) into the toothing of the threaded rod (3) is configured as a ratchet mechanism. The engagement elements (2a, 1a) of the rotary sleeve (2) and guide sleeve (1) interact with the teeth of the threaded rod (3) in such a way that a clicking sound is generated when a specified dose is delivered and when a specified dose is dispensed.

In order to prevent a further dose from being set up when the last dose has been dispensed, the rotary sleeve (2) has a rotational stop sleeve stop (not visible) which may come into abutting contact with a threaded rod stop (3c) that is furnished on the threaded rod (3). The injection device further comprises a metering sleeve (4). The metering sleeve (4) is mounted in a rotationally fixed and axially movable manner relative to the housing (6) of the injection device via a metering bridge (4a) by means of a guide sleeve groove (not shown) of the guide sleeve (1). The user may move the metering sleeve (4) axially back and forth by means of a metering knob (5) arranged at the proximal end of the metering sleeve (4), which is axially fixedly connected to a metering sleeve ring groove (4c) of the metering sleeve (4) via a metering knob bridge (not shown). To display the individual metering movements, the metering sleeve (1) preferably has a display (not shown). The display (not shown) of the metering sleeve (1) may be seen via a housing window (6b) furnished on the housing (6); the user may thus see the position of the injection device. The metering sleeve (4) is connected to the rotary sleeve (2) via a threaded connection. The inside of the metering sleeve (4) comprises a metering sleeve thread (4b) that engages with the rotary sleeve thread (2b) on the outside of the rotary sleeve (2). The injection device further comprises a locking ring (11) having at its distal end a ratchet tooth (11a) that is connected to the guide sleeve (1) by means of a locking arm (11b) of the locking ring (11). The ratchet tooth (11a) of the locking ring (11) may engage in a ratchet tooth (1g, see e.g. FIG. 2f) of the guide sleeve (1); the ratchet tooth (1a) of the guide sleeve (1) and the ratchet toothing (1g, see e.g. FIG. 2f) of the guide sleeve (1) are formed in such a way that the ratchet tooth (11a) may move in a first direction of rotation relative to the ratchet toothing (1g, see e.g. FIG. 2f) of the guide sleeve (1) via the ratchet toothing (1g, see e.g. FIG. 2f), and a relative rotation between the locking ring (11) and the guide sleeve (1) in a direction of rotation opposite the first rotation direction, namely in a second direction of rotation, may be prevented. The locking ring may not be pushed in the axial direction relative to the housing (6) or the guide sleeve (1). Further, the locking ring (11) comprises a coupling toothing (11c) on its inner circumferential surface which may engage with a counter-coupling toothing (2e) arranged on the outer circumferential surface of the engaging element (2a) of the rotary sleeve (1). An abutment surface (11d) is arranged at the proximal end of the locking ring (11) and may come into abutting contact with a distal side of the rotary sleeve ring bridge (2c).

FIG. 2a shows a longitudinal cross section of the first embodiment of the carpoule holder in an initial position, in which the carpoule has not been received in the carpoule holder. The holding element (9) is inserted in the carpoule holder (8). As shown in FIG. 2c, the projection (9a) of the holding element (9) extends into a recess (8c) of the carpoule holder housing (8d) of the carpoule holder (8). The cam (9b) of the holding element (9) rests against the inner circumferential surface of the carpoule holder (8) in a radially elastic manner. The holding element (9) is kept in the carpoule holder (8), elastically relaxed in the axial direction. The brackets (9h) are connected to one another via connecting bridges (9i) and are fastened via connecting bridges (9i) to the first (9f) or second spring seat (9g).

The holding element (9) is inserted into the carpoule holder in such a way that a carpoule (10) may be introduced into the carpoule holder (8), and particularly into the carpoule holder housing (8d) of the carpoule holder (8). The carpoule (10) is pushed into the carpoule holder (8) through a proximal opening of the carpoule holder housing (8d) of the carpoule holder (8). As FIG. 2b shows, preferably the distal end of the carpoule (10) may come into axial abutting contact with the carpoule holder housing (8d) at a distal end of the carpoule holder (8). The holding element (9) is in the first position. The holding element (9) is arranged in an annular gap between the carpoule holder (8) and the carpoule (10). The clamping element (9d) of the spring element (9c) of the holding element (9) protrudes in the proximal direction over the proximal edge (10a) of the carpoule (10). In order to hold the carpoule (10) fixedly in the carpoule holder (8), an axial force may act in the distal direction on the second spring seat (9g) in such a way that the holding element (8) is elastically tensioned and is pushed in the axial direction relative to the carpoule holder housing (8d) of the carpoule holder (8). As shown from FIGS. 2d and 2e, the projection (9a) of the holding element (9) moves out of engagement with the recess (8c) of the carpoule holder (8), and the cam (9b) thus comes into engagement with the recess (8c) of the carpoule holder (8). The spring element (9c) of the holding element (9) is thereby tensioned radially inward so that the clamping element (9d) holds or clasps the proximal edge (10a) of the carpoule (10). At the distal end, the carpoule (10) is supported on or in the carpoule holder (8); at the proximal end, it is supported on the holding element (9), and particularly the clamping element (9d) of the holding element (9). As shown in FIG. 2f, the carpoule holder (8) connected to the carpoule (10) may now be connected axially to the housing (6) of the injection device. The housing guide ring (6d) of the housing (6) is engaged with the carpoule holder guide groove (8e) of the carpoule holder (8). The carpoule holder (8) may be adhered or welded to the housing (6) of the injection device. Other forms of fastening the carpoule holder (8) and the housing (6), for example using other fastening means, may also be provided. Preferably, adhesive or an alternative fastening means may be applied between the axially extending housing bridges (6e) of the housing (6) of the injection device, in order to better attach the carpoule holder (8) to the housing (6) of the injection device. Alternatively, the carpoule holder (8) may have a carpoule holder bridge, and preferably a plurality of carpoule holder bridges extending in the axial direction, between which adhesive or an alternative fastening means is applied. Alternatively, carpoule holding rings may be furnished on the carpoule holder (8), and housing bridges (6e) may be furnished on the housing (6) of the injection device.

FIG. 2f depicts a longitudinal cross section of the first embodiment of the injection device with a metering sleeve (4) in an initial position. The metering sleeve (4), which is mounted in the housing (6) in such a way that it may move axially and is rotationally fixed, is inserted into the injection device, and the display (not shown) attached to the metering sleeve (4) is visible through the housing window (6b) and indicates to the user that the injection device is in the initial position. The metering sleeve (4) is in a threaded engagement with the rotary sleeve thread (2b) of the rotary sleeve (2), via the metering sleeve thread (4b). A radially outwardly protruding projection (not shown) of the rotary sleeve (2) is in abutting contact, in particular in rotary abutting contact, with a first radially inwardly projecting projection (not shown) of the guide sleeve (1).

A head (not shown), deployed on the engaging element (2a) of the rotary sleeve (2), engages with the toothing of the threaded rod (3). To this end, the head (not shown) of the engagement element (2a) of the rotary sleeve (2) engages between two adjacent teeth (3a) into a tooth gap (not shown) of the threaded rod (3), i.e. between a steep flank (not shown) of a tooth (3a) and a flat flank (not shown) of an adjacent tooth (3a) of the threaded rod (3). Further, a head (not shown) provided on the insertion element (1a) of the guide sleeve (1) likewise engages with the toothing of the threaded rod (3). To this end, the head (not shown) of the engagement element (1a) of the guide sleeve (1) also engages between two adjacent teeth (3a) into a tooth gap (not shown) of the threaded rod (3). The head (not shown) of the engagement element (1a) of the guide sleeve is located between a steep flank (not shown) of a tooth (3a) and a flat flank (not shown) of an adjacent tooth (3a) of the threaded rod (3).

To adjust or draw a dose, the user pulls the metering knob (5) in the proximal direction. The metering sleeve (4) is thereby pushed axially in the proximal direction. Because of the threaded engagement between the metering sleeve (4) and the rotary sleeve (2), the rotary sleeve (2) rotates in the first direction of rotation until the projection (not shown) of the rotary sleeve (2) comes into abutting contact with a second radially inwardly projecting projection (not shown) of the guide sleeve (1). The flat flank (not shown) of the head (not shown) of the engagement element (2a) of the rotary sleeve (2) slides over the flat flank (3a') of the tooth (3a) of the threaded rod (3) and thereby reaches an adjacent tooth gap (not shown). The steep flank (not shown) of the head (not shown) of the engaging element (1a) of the guide sleeve (1) is in abutting contact with the steep flank (not shown) of the tooth (3a) of the threaded rod (3), so that the threaded rod (3) is held rotationally fixed. The display (not shown) attached to the metering sleeve (4) indicates to the user via the housing window (6b) that the injection device is in the drawn position.

When setting up or drawing a dose, the engagement element (2a) of the rotary sleeve (2) is radially deflected. The counter-coupling toothing (2e) of the rotary sleeve (2) then engages with the coupling toothing (11c) of the locking ring (11). The locking ring (11) and the rotary sleeve (2) are rotated in the first rotation direction relative to the housing (6) or the guide sleeve (1) by the coupling of the rotary sleeve (2) to the locking ring (11). The ratchet tooth (11a) of the locking ring (11) slides over the ratchet toothing (1g) of the guide sleeve (1). The ratchet tooth (11a) of the locking ring (11) may slide over the ratchet toothing (1g) of the guide sleeve (1) only in the first rotation direction relative to the guide sleeve (1), while preventing relative rotation in the second rotation direction. The engagement element (2a) of the rotary sleeve (2) is radially deflected until the head (not shown) of the engagement element reaches the tooth gap (3a') of the threaded rod (3) or until a fixed dose is completely dispensed or drawn.

By this means, the dispensing of an incompletely set up or drawn dose may be prevented.

The drawing motion of the metering sleeve (4) and the dispensing motion of the threaded rod (3) are translated into one another. The thread pitch of the threaded connection (4b, 2b) between the metering sleeve (4) and the rotary sleeve (2) is greater than the thread pitch of the threaded connection (3b, 1e) between the threaded rod (3) and the guide sleeve (1).

To dispense a specified dose, the user pushes the dispensing knob (5) in the distal direction, pushing the metering sleeve (4) axially in the distal direction. The rotary sleeve (2) rotates in the direction opposite the first rotation direction, i.e. in the second rotation direction, until the projection (not shown) of the rotary sleeve (2) comes into abutting contact with the first radially inwardly projecting projection (not shown) of the guide sleeve (1). The steep flank (not shown) of the head (not shown) of the engaging element (2a) of the guide sleeve (2) is in abutting contact with the steep flank (not shown) of the tooth (3a) of the threaded rod (3), and transmits a rotational moment to the threaded rod (3). The threaded rod (3) is consequently screwed in the distal direction by the threaded connection between the internal thread (1e) of the guide sleeve (1) and the external thread (3b) of the threaded rod (3). To this end, the head (not shown) of the engagement element (2a) of the rotary sleeve (2) slides axially along the tooth gap (not shown) of the threaded rod (3). The coupling toothing (11c) of the locking ring (11) is uncoupled from the countercoupling toothing (2e) of the rotary sleeve (2) so that the rotary sleeve (2) may rotate in the second rotation direction relative to the locking ring (11). The ratchet tooth (11c) of the locking ring (11) projects into the ratchet toothing (1g) of the guide sleeve (1). The flat flank of the head (not shown) of the rotary sleeve (1) slides over the flat flank of the tooth (3a') of the threaded rod (3). A plug (10a) received by a carpoule (10) is pushed in the distal direction by means of a flange (7) axially fixedly attached to the threaded rod (3). The plug (10b) may press out the fluid product out via an injection needle (not shown) attached to the carpoule holder.

After the last dose has been dispensed from the injection device, two rotary sleeve stops (not shown) of the rotary sleeve (2) are in abutting contact with the corresponding two threaded rod stops (3c) of the threaded rod (3). Thus, no further dose may be drawn via the metering sleeve (4), because rotation of the rotary sleeve (2) is blocked.

FIG. 3 depicts an exploded view of a second embodiment of the injection device according to this invention. The injection device differs essentially from the injection device of the first embodiment only with respect to the holding element (9). As shown in FIG. 4a, the holding element (9') comprises a first spring seat (9f') and a second spring seat (9g') and a ring element (9e'); the first spring seat (9f') is connected to the second spring seat (9g') via the plurality of brackets (9h') and the plurality of connecting bridges (9i'). An outwardly projecting cam (9b') is arranged on the second spring seat (9g'). An inwardly projecting clamping element (9d') is furnished on the ring element (9e').

As shown in FIGS. 4b and 4c, the carpoule (10) is first placed in the carpoule holder (8), so that the carpoule (10) and the carpoule holder (8) are in axial abutting contact on the distal end. Thereafter, the holding element (9') is then introduced into the carpoule holder (8) in such a way that the holding element (9') is arranged in an annular gap between the carpoule holder (8) and the carpoule (10). The holding element (9') is pushed into the carpoule holder housing (8d) by means of an axial force that acts on the second spring seat (9g') in the distal direction, relative to the carpoule holder housing (8d). As shown in FIGS. 4d and 4e, the cam (9b') of the holding element (9') engages with the recess (8c) of the carpoule holder (8). Further, the clamping element (9d') of the holding element (9') holds or clasps the proximal edge (10a) of the carpoule (10). In this case, the holding element (9') is kept tensioned in the distal direction by means of the engagement between the cam (9b') and the recess (8c). The carpoule (10) is supported in the carpoule holder (8) by means of the holding element (9'). As shown in FIG. 4f, the carpoule holder (8) connected to the carpoule (10) may now be fixedly connected axially to the housing (6) of the injection device. The carpoule holder (8) may be adhered or welded to the housing (6) of the injection device. Other forms of fastening the carpoule holder (8) and the housing (6), for example using other fastening means, may also be provided. Preferably, adhesive or an alternative fastening means may be applied between the axially extending housing bridges (6e) of the housing (6) of the injection device, in order to better attach the carpoule holder (8) to the housing (6) of the injection device. Alternatively, the carpoule holder (8) may have a carpoule holder bridge, and preferably a plurality of carpoule holder bridges extending in the axial direction, between which adhesive or an alternative fastening means is applied. Alternatively, carpoule holding rings may be furnished on the carpoule holder (8) and housing bridges (6e) may be furnished on the housing (6) of the injection device.

Figure 6E:
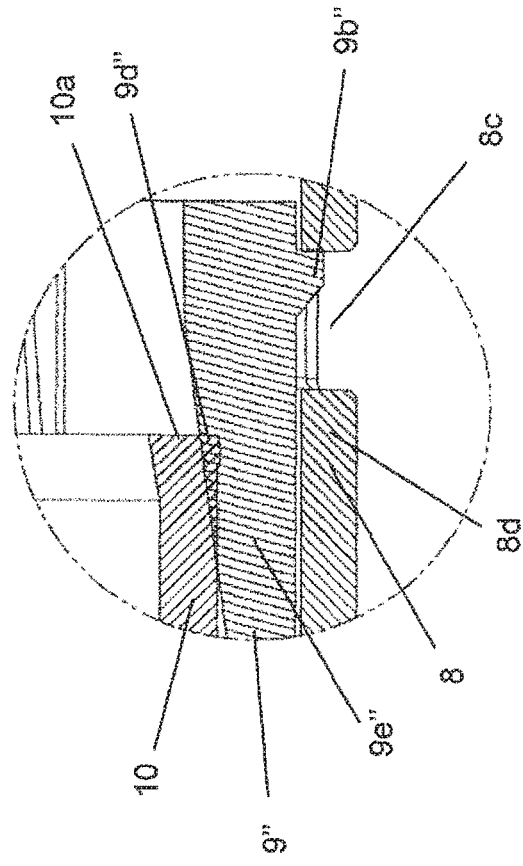
FIG. 6e is a detail view of FIG. 6d.

FIG. 5 shows an exploded view of a third embodiment of the injection device according to this invention. The injection device differs essentially from the injection device of the first embodiment only with respect to the holding element (9"). As shown in FIG. 6a, the holding element (9") is realized as a cylindrical ring element (9e"). As shown in FIGS. 6b and 6c, the carpoule (10) is first placed in the carpoule holder (8), and the carpoule holder (8) has a recess (8c). The carpoule (10) and the carpoule holder (8) come into axial abutting contact at the distal end. Thereafter, the holding element (9") may be inserted into a carpoule holder (8) that has received the carpoule (10), and specifically into a ring gap between the carpoule (10) and the carpoule holder (8), in the distal direction. For this purpose, an axial force may act in the distal direction on the proximal end of the ring element (9e") of the holding element (9"). As shown in FIGS. 6d and 6e, an outward-projecting cam (9b") of the ring element (9e") may then protrude outward into the recess (8c) of the carpoule holder housing (8d) of the carpoule holder (8). An inwardly projecting clamping element (9d") of the ring element (9e") of the holding element (9") clamps the proximal edge (10a) of the carpoule (10).

Figure 6F:
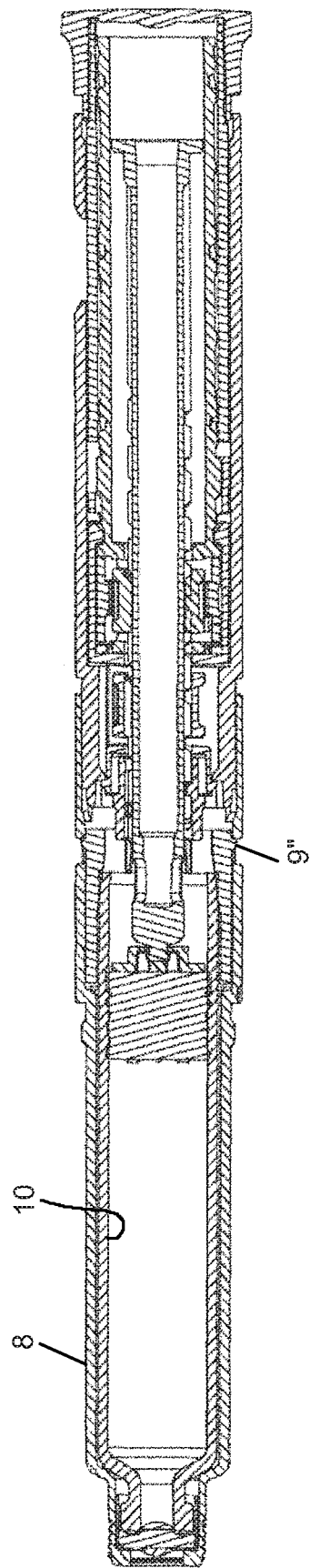
FIG. 6f is a longitudinal cross section of the injection device with the third embodiment of the carpoule holder in which the carpoule has been received and fastened, wherein the carpoule holder is axially fixedly connected to the housing of the injection device for metering and administering a fixed dose of a fluid product.

The carpoule (10) is accommodated in the carpoule holder (8) so as to be axially fixed by means of this clamping fit or clamping seat. At the distal end, the carpoule (10) is supported on or in the carpoule holder (8); at the proximal end, it is supported on the holding element (9"), and in particular on the clamping element (9d"). As shown in FIG. 6f, the carpoule holder (8) connected to the carpoule (10) may now be connected axially to the housing (6) of the injection device. The carpoule holder (8) may be adhered or welded to the housing (6) of the induction device. Other forms of fastening the carpoule holder (8) and the housing (6), for example using other fastening means, may also be provided. Preferably, adhesive or an alternative fastening means may be applied between the axially extending housing bridges (6e) of the housing (6) of the injection device, in order to better attach the carpoule holder (8) to the housing (6) of the injection device. Alternatively, the carpoule holder (8) may have a carpoule holder bridge, and preferably a plurality of carpoule holder bridges extending in the axial direction, between which adhesive or an alternative fastening means is applied. Alternatively, carpoule holding rings may be furnished on the carpoule holder (8) and housing bridges (6e) may be furnished on the housing (6) of the injection device.

FIG. 7 shows an exploded view of a fourth embodiment of the injection device according to this invention. The injection device differs essentially from the injection device of the first embodiment only with respect to absence of the holding element (9, 9', 9"). As shown in FIG. 8a, the carpoule (10) is inserted into the carpoule holder (8) until the carpoule (10) comes into distal abutting contact with the carpoule holder (8), as depicted in FIG. 8b. As shown in FIG. 8c, the carpoule holder (8) comprises a recess (8c) in the carpoule holder housing (8d). As shown in FIGS. 8d and 8e, to fix the carpoule (10) in place within the carpoule holder (8), an adhesive (12) or other fastening means is introduced through the recess (8c) of the carpoule holder housing (8d) in such a way that the carpoule (10) is held axially fixed in the carpoule holder. The adhesive (12) or fastening means may be applied in the form of one or more drops. Alternatively, a weld connection may be furnished between the carpoule (10) and the carpoule holder (8). The carpoule (10) is held at the distal end on or in the carpoule holder (8) and is attached at the proximal end to the carpoule holder. The fastening of the carpoule (10) to the carpoule holder (8) may preferably take place between the carpoule holder housing (8d) and the side wall of the carpoule (10). Alternatively, the fastening may take place between the proximal edge (10a) of the carpoule (10) and the carpoule holder housing (8d) of the carpoule holder (8). As shown in FIG. 8f, the carpoule holder (8) connected to the carpoule (10) may now be fixedly connected axially to the housing (6) of the injection device. The carpoule holder (8) may be adhered or welded to the housing (6) of the injection device. Other forms of fastening the carpoule holder (8) and the housing (6), for example using other fastening means, may also be provided. Preferably, adhesive or an alternative fastening means may be applied between the axially extending housing bridges (6e) of the housing (6) of the injection device, in order to better attach the carpoule holder (8) to the housing (6) of the injection device.

Alternatively, the carpoule holder (8) may have a carpoule holder bridge, and preferably a plurality of carpoule holder bridges extending in the axial direction, between which adhesive or an alternative fastening means is applied. Alternatively, carpoule holding rings may be furnished on the carpoule holder (8) and housing bridges (6e) may be furnished on the housing (6) of the injection device.

What is claimed is:

1. A device comprising a carpoule holder for receiving a carpoule and for fastening to a drive mechanism and/or to a metering mechanism and/or to a housing of an injection device, comprising:
   an elastically deformable holding element for fastening the carpoule onto or in the carpoule holder,
   wherein the holding element comprises a cam and a clamping element, wherein the cam engages in a recess of the carpoule holder so as to elastically tension the holding element, and wherein the clamping element projects radially inward, in order to hold, clamp, or grasp a surface of the carpoule inserted into the carpoule holder, and
   wherein the holding element is configured to be connected to the carpoule holder and received completely by the carpoule holder.

2. The device of claim 1, wherein the holding element comprises a projection and a spring element.

3. The device of claim 2, wherein the projection and the clamping element are provided on the spring element.

4. The device of claim 1, wherein the carpoule holder comprises a carpoule holder housing.

5. The device of claim 4, wherein the carpoule holder housing comprises a recess.

6. The device of claim 1, wherein the holding element comprises a ring element.

7. The device of claim 6, wherein the ring element comprises a first spring seat, and a second spring seat.

8. The device of claim 7, wherein the cam is arranged on one of the spring seats.

9. The device of claim 7, wherein the ring element comprises a plurality of brackets and a plurality of connecting bridges and the first spring seat is connected to the second spring seat via the plurality of brackets and the plurality of connecting bridges.

10. The device of claim 1, wherein in a first position, the carpoule is movably received in the carpoule holder, and the holding element is arranged at least partially in an annular gap between the carpoule holder and the carpoule.

11. The device of claim 10, wherein in the first position, a projection of the holding element protrudes into a recess of the carpoule holder so as to connect the holding element to the carpoule holder.

12. The device of claim 10, wherein in a second position, in which the carpoule is received and fastened in the carpoule holder, the holding element is arranged at least partially in the annular gap between the carpoule holder and the carpoule.

13. The device of claim 12, wherein the holding element is configured such that in the second position, the holding element holds the carpoule axially fixedly relative to the carpoule holder.

14. The device of claim 12, wherein in the second position, the cam of the holding element protrudes into the recess of the carpoule holder so as to elastically tension the holding element.

15. The device of claim 14, wherein in the second position, the clamping element of the holding element holds or clasps a proximal end of the carpoule.

16. A method of assembling a carpoule to or in a device comprising a carpoule holder, comprising:
    fitting a projection of a holding element into a recess of the carpoule holder;
    inserting the carpoule into the carpoule holder; and
    shifting the holding element in a distal direction such that the projection of the holding element is moved out of the recess of the carpoule holder and a cam of the holding element is moved into the recess of the carpoule holder, whereby the holding element is elastically tensioned and the carpoule is connected fixedly to the carpoule holder by a clamping element of the holding element holding or clasping a surface of a proximal end of the carpoule.

17. The method of claim 16, wherein the holding element further comprises a ring element.

18. The method of claim 17, wherein the ring element comprises a first spring seat, and a second spring seat.

19. The method of claim 18, wherein the cam is arranged on one of the spring seats.

20. The method of claim 18, wherein the ring element comprises a plurality of brackets and a plurality of connecting bridges and the first spring seat is connected to the second spring seat via the plurality of brackets and the plurality of connecting bridges.

* * * * *